US008288437B2

(12) United States Patent
Heiman et al.

(10) Patent No.: US 8,288,437 B2
(45) Date of Patent: Oct. 16, 2012

(54) SALTS, AQUEOUS LIQUID COMPOSITIONS CONTAINING SALTS OF ABSCISIC ACID ANALOGS AND METHODS OF THEIR PREPARATION

(75) Inventors: Daniel F. Heiman, Libertyville, IL (US); Benjamin A. Belkind, Wilmette, IL (US); Zhengyu Huang, Buffalo Grove, IL (US); Xiaozhong Liu, Vernon Hills, IL (US); Peter D. Petracek, Grayslake, IL (US)

(73) Assignee: Valent BioSciences Corporation, Libertyville, IL (US)

( * ) Notice: Subject to any disclaimer, the term of this patent is extended or adjusted under 35 U.S.C. 154(b) by 547 days.

(21) Appl. No.: 12/508,133

(22) Filed: Jul. 23, 2009

(65) Prior Publication Data

US 2010/0022391 A1 Jan. 28, 2010

Related U.S. Application Data

(60) Provisional application No. 61/083,203, filed on Jul. 24, 2008.

(51) Int. Cl.
*A61K 31/19* (2006.01)
*C07C 59/205* (2006.01)
*C07C 62/18* (2006.01)
*C07C 62/30* (2006.01)

(52) U.S. Cl. ......... 514/557; 562/462; 562/508; 562/510
(58) Field of Classification Search .................. None
See application file for complete search history.

(56) References Cited

U.S. PATENT DOCUMENTS

| 4,209,530 | A | 6/1980 | Visscher |
| 4,434,180 | A | 2/1984 | Visscher |
| 4,581,057 | A | * | 4/1986 | Nooden ............................. 71/28 |
| 5,201,931 | A | 4/1993 | Abrams et al. |
| 5,518,995 | A | 5/1996 | Abrams et al. |
| 6,004,905 | A | 12/1999 | Abrams et al. |
| 6,051,533 | A | 4/2000 | Kajikawa et al. |
| 6,200,929 | B1 | 3/2001 | Horibe et al. |
| 2004/0023938 | A1 | 2/2004 | Tabuchi et al. |
| 2005/0164359 | A1 | 7/2005 | Hashimoto et al. |
| 2006/0276339 | A1 | 12/2006 | Windsor et al. |
| 2007/0049496 | A1 | 3/2007 | Messerschmidt et al. |
| 2007/0066485 | A1 | 3/2007 | Rademacher et al. |
| 2007/0082819 | A1 | 4/2007 | Perry et al. |
| 2008/0108115 | A1 | 5/2008 | Bringi et al. |

FOREIGN PATENT DOCUMENTS

| GB | 1251867 | 11/1971 |
| WO | WO 2005/115144 A1 | 12/2005 |

OTHER PUBLICATIONS

Asami et al, RIKEN Review, Abscisic Acid Analogs Possessing Hetero Five-membered Ring: Design, Synthesis and Activity, 1999, 21, pp. 17-19.*
Tadeo Asami et al, Plant Cell Physiology, Biologic Activities of an Abscisic Acid Analog in Barley, Cress and Rice, 1998, 39(3), pp. 342-348.*
Mauseth, "Botany an introduction to plant biology", 1991 Philadelphia Saundera pp. 348-415.
Raven et al., Biology of plants fifth edition, 1992 New York Worth. pp. 545-572.
Milborrow, "The chemistry and physiology of abscisic acid", Am. Rev. Plant Physiol, 1974, 25 pp. 259-307.
Railton et al., "Effects of abscisic acid on the levels of endogenous gibberellins-like substances in Solanum andigena", 1973 Planta (Berl.) 112, pp. 65-69.
Bonnafous et al., "Nouvelle methode de resolution optique de l'acide abscisique", 1973 Tetrahedron Letters No. 13, pp. 1119-1122.
Finkelstein et al., "Abscisic Acid Biosynthesis and Response", 2002 The Arabidopsis Book, American Society of Plant Biologists, pp. 1-52.
Balsevich et al., "Preparation and Analysis of Some Acetosugar Esters of Abscisic Acid and Derivatives", Can. J. Chem., 1996, pp. 238-245.

* cited by examiner

*Primary Examiner* — Paul A Zucker
(74) *Attorney, Agent, or Firm* — Wood, Phillips, Katz, Clark & Mortimer

(57) ABSTRACT

The present invention generally relates to salts of abscisic acid analogs, aqueous liquid compositions containing salts of analogs of abscisic acid and methods of their preparation for agricultural use.

12 Claims, No Drawings

US 8,288,437 B2

SALTS, AQUEOUS LIQUID COMPOSITIONS CONTAINING SALTS OF ABSCISIC ACID ANALOGS AND METHODS OF THEIR PREPARATION

FIELD OF THE INVENTION

The present invention generally relates to salts of abscisic acid analogs, aqueous liquid compositions containing salts of abscisic acid analogs having enhanced biological activity and methods of their preparation for agricultural use.

BACKGROUND OF THE INVENTION

Abscisic acid is a naturally occurring plant hormone which acts primarily to inhibit growth of plants, maintain dormancy of buds, inhibit fruit-ripening, activate the pathogen resistance response defense, induce senescence in already-damaged cells and their proximate neighbors, and help the plant tolerate stressful conditions. See Arteca, R. (1996), *Plant Growth Substances: Principles and Applications*. New York: Chapman & Hall; Mauseth, J. D. (1991), *Botany. An Introduction to Plant Biology*. Philadelphia: Saunders. pp. 348-415; Raven, P. H., Evert, R. F., and Eichhorn, S. E. (1992), *Biology of Plants*. New York: Worth. pp. 545-572.

Abscisic acid owes its name to the belief that this plant growth regulator causes the abscission of leaves from deciduous trees in the fall. Absicin II and dormin are names previously used for this plant hormone. The chemistry and physiology of abscisic acid and its analogs is described by Milborrow, Ann. Rev. Plant Physiol. 1974, 25, 259-307.

Abscisic acid analogs are structural derivatives of 2-cis-, 4-trans-(S)-(+)-abscisic acid. An extensive series of analogs of abscisic acid has been prepared by researchers at the Plant Biotechnology Institute of the National Research Council of Canada, Saskatoon, Saskatchewan. Some of these abscisic acid analogs are disclosed in U.S. Pat. Nos. 5,201,931, 5,518, 995 and 6,004,905, which are incorporated herein by reference. Presently preferred abscisic acid analogs include PBI-376, PBI-524, PBI-697 and PBI-410.

Prior art (U.K. Pat. No. 1251867 and Railton and Wareing, Planta 112, 65-69, 1973) taught, inter alia, preparation of amine salts of racemic abscisic acid. A salt of racemic (R,S)-(±)-2-trans-,4-trans-abscisic acid with the chiral alkaloid brucine was prepared as a means of resolving a small quantity of the racemate in order to study the physical properties of its enantiomers (J. C. Bonnafous, et al., Tetrahedron Letters, 1119-1122, 1973). Salts of (S)-(+)-abscisic acid are disclosed in co-pending U.S. patent applications Ser. No. 12/011,846 filed Jan. 30, 2008 entitled SALTS, AQUEOUS LIQUID COMPOSITIONS CONTAINING SALTS OF S-(+)-ABSCISIC ACID and Ser. No. 12/011,845 filed Jan. 30, 2008 entitled SALTS, AQUEOUS LIQUID COMPOSITIONS CONTAINING SALTS OF ABSCISIC ACID ANALOGS AND METHODS OF THEIR PREPARATION, and in a co-pending patent application No. 61/083,202 filed on the same day as this application. Contents of these patent applications are herein incorporated by reference. However, these patent applications do not disclose salts of abscisic acid analogs having substantially enhanced biological activity relative to 2-cis-,4-trans-(S)-(+)-abscisic acid itself, nor do they disclose salts of abscisic acid analogs having substantially enhanced biological activity relative to the abscisic acid analogs themselves.

As noted above, abscisic acid analogs are carboxylic acids, and thus in a medium having an acidic pH, they are protonated and in their neutral undissociated form. This uncharged, undissociated form is more lipophilic than a salt of an abscisic acid analog, and penetration of the uncharged acid form into the plant cuticle would be favored relative to the charged, dissociated form of the abscisic acid analog present at higher pH (Blumenfeld and Bukovac 1972, Planta 107: 261-268). The uncharged, undissociated form of the abscisic acid analog would be expected to cross cell membranes from the apoplast into the cytosol more easily than a salt form would. In spite of this, we have surprisingly found that treatments comprising certain salts of abscisic acid analogs of this invention have substantially better biological activity when compared with similar treatments comprising the acid form of the same abscisic acid analog at the same concentration. We have also surprisingly found that certain iodide salts, when applied to plants in combination with the same abscisic acid analog, produce substantially enhanced biological activity.

Abscisic acid was first defined in the early 1960s as a growth inhibitor accumulating in abscising cotton fruit and in leaves of sycamore trees photoperiodically induced to become dormant. See, Finkelstein R R, Rock C D (2002), *Abscisic Acid Biosynthesis and Response*, The Arabidopsis Book: Vol. 45, No. 1 pp. 1-48. Since then, abscisic acid has been shown to regulate many aspects of plant growth and development, including embryo maturation, seed dormancy, germination, cell division and elongation, etc. Although abscisic acid has historically been thought of as a growth inhibitor, young tissues have high abscisic acid levels, and abscisic acid-deficient mutant plants are severely stunted because their ability to reduce transpiration and establish turgor is impaired. Exogenous abscisic acid treatment of mutants restores normal cell expansion and growth.

Abscisic acid is thought to initiate its effects on cells through binding to receptor proteins, although their identities and locations are still largely unknown. Activation of the putative receptor(s) causes a chain of events that results in rapid changes in ion channels and slower changes in the pattern of gene transcription. While many individual components of this chain of events have been identified, a complete picture has not yet been obtained.

Commercial formulations comprising abscisic acid are used in agriculture for various purposes, such as improving stress tolerance, slowing growth rate, adjusting flowering phase, and other purposes. Abscisic acid has also been reported to possess insect inhibition qualities. See U.S. Pat. Nos. 4,434,180 and 4,209,530 to Visscher. Abscisic acid in a powdered form is currently commercially available from Lomon Biotechnology Company, Ltd., a Chinese company, which markets it as a substance that, among other uses, improves the yield and quality of crops.

However, one of the problems associated with preparation of formulations of abscisic acid analogs is their relatively poor solubility in water: The solubilities of these compounds in water are even lower than that of (S)-(+)-abscisic acid itself, and for (S)-(+)-abscisic acid not more than about 3 grams per liter or alternatively, less than 0.3% by weight will dissolve at ordinary temperatures. Stated differently, a concentration of about 3000 parts per million (ppm) is the highest concentration of (S)-(+)-abscisic acid that can be achieved in pure water at room temperature, and the maximum for abscisic acid analogs is even lower. While abscisic acid analogs have better solubility in some organic solvents, liquid formulations of abscisic acid analogs in organic solvents are unacceptable in some contexts because of flammability, toxicity, or pollution considerations. For example, the Environmental Protection Agency of the U.S. state of California is currently requiring that liquid formulations of agricultural products contain no volatile organic solvent, and several other U.S.

states are considering similar regulations. Nonvolatile organic solvents have the detriment that, since they do not evaporate, they remain in the agricultural product as it impinges upon and is absorbed into the target plant, with a probability of causing phytotoxicity and contaminating food products, since the amount of the solvent greatly exceeds the amount of active ingredient applied.

A further problem observed with concentrated solutions of abscisic acid analogs in organic solvents is that it is difficult to prepare more dilute solutions by dilution into water without having a portion of the abscisic acid analog precipitate out in a gummy form that redissolves only very slowly and with great difficulty. This is of practical importance because a major use of abscisic acid analogs in agriculture or horticulture is for the reduction of transpiration in nursery plants being prepared for transplantation or for sale to consumers, for which purpose the abscisic acid analog may be applied by means of an injection system and automatic or hand applicators. The solution for use in such an applicator must be a concentrate between about 50 and 100 times more concentrated than the dose rate that is actually reaching the plants when they are treated by foliar spray or drench. Thus for a typical application to the nursery plants of 60 to 600 ppm, the concentrate must contain between 3000 and 60,000 ppm of (S)-(+)-abscisic acid in a solution that will mix instantly and completely with the water flowing through the hose, in such a way that there is no possibility of formation of a precipitate that would clog the nozzle through which the water containing active ingredient is applied to the plants or the growing media of the plants. As explained above, the solubility of abscisic acid analogs in water is less than 3000 ppm at ordinary ambient temperature, so such an intermediate solution cannot practically be prepared in water. A solution of an abscisic acid analog in an organic solvent cannot be used in such an injection applicator, because precipitation of the active ingredient will occur during the mixing into the water flowing in the system, and the spray nozzle will be clogged. Because of the solubility limitation, it is also not possible to provide a liquid formulation of the abscisic acid analog in organic solvent at a higher concentration (e.g. 10%) and then at the time of application to prepare an intermediate dilution in water to achieve the desired concentration of 3,000 to 60,000 ppm in the reservoir of the injection applicator.

An identical problem arises in the case of application of an abscisic acid analog to a vineyard, orchard or agricultural field through an irrigation system, a practice commonly known as chemigation. Again, such a system requires a concentrated solution of the active ingredient in a liquid solvent in such a form such that that solution is instantly and completely miscible with a stream of water flowing through the irrigation system. If any precipitation were to occur, it would block the nozzles (known as emitters) through which the water and dissolved active ingredient reach the target plants. Again in this situation a formulation consisting of an organic solution of the abscisic acid analog would not be acceptable because of the problem of the low water solubility.

Abscisic acid analogs are very expensive. They can be manufactured only by multi-step chemical synthesis, involving costly reagents and several laborious purifications. When these abscisic acid analogs are applied to plants, uptake is poor, so a large excess must be employed. It is possible to improve uptake of the abscisic acid analogs by combining them with various surfactants; however, it is well known that the use of surfactants can damage the foliage, flowers and fruits of sensitive plants, producing phytotoxicity and reducing the value or destroying the crop.

While powdered formulations of abscisic acid analogs could be prepared, it is often more convenient to use concentrated liquid solutions instead of powders. Therefore, there is an unmet need in the art for highly efficacious abscisic acid analog formulations comprising salts of abscisic acid analogs, which are much more soluble in water than the acids themselves are and do not require that surfactants be employed to promote their uptake by plants.

SUMMARY OF THE INVENTION

The present invention is generally directed to salts of abscisic acid analogs prepared with alkali metal cations of high molecular weight or large steric bulk.

In a further embodiment, the present invention is generally directed to aqueous compositions comprising an effective amount of a salt of an analog of abscisic acid prepared with alkali metal cations of high molecular weight or large steric bulk wherein the concentration of the salt is at least about 0.5% by weight of the aqueous composition. Applicants have unexpectedly discovered that salts of abscisic acid analogs prepared with alkali metal cations of high molecular weight or large steric bulk allow for dramatic increases in solubility of abscisic acid analogs in water so that concentrated solutions can be obtained and at the same time provide substantially enhanced biological activity relative to the acids themselves. As a result of Applicants' invention, solutions can be obtained with abscisic acid analog concentrations as high as about 50% by weight. The present invention allows for the creation of concentrated formulations of abscisic acid analogs that are convenient for packaging, storage, transport and handling, but must be diluted prior to use and specifically allows any arbitrary intermediate dilution of these formulations to be made into water without the risk of precipitation of the active ingredient.

Compositions of the present invention generally comprise the salt, an antimicrobial and optionally a surfactant. Other components that enhance the long-term storage stability of the composition or the biological activity of the abscisic acid analog may optionally be included.

Some of the suitable salts of the invention include, but are not limited to, the rubidium or cesium salts, organic quaternary ammonium salts, guanidinium salts or mixtures comprising any number of these. In one embodiment, the organic quaternary ammonium salt is the tetramethylammonium salt. In another embodiment, the organic quaternary ammonium salt is the tetrabutylammonium salt. In another embodiment, the organic quaternary ammonium salt is the choline salt. In yet another embodiment, the guanidinium salt is the tetramethylguanidinium salt. These examples of salts are not limiting as other salts may also be suitable for use the present invention. One presently preferred salt is the choline salt.

The present invention is also directed to methods of preparation of aqueous compositions comprising salts of an abscisic acid analog prepared with alkali metal cations of high molecular weight or large steric bulk. In one embodiment, the invention is directed to a method of preparation of the rubidium salt of the abscisic acid analog comprising reacting the abscisic acid analog with a chemically equivalent amount of rubidium hydroxide, rubidium bicarbonate or rubidium carbonate in aqueous solution. In another embodiment, the invention is directed to a method of preparation of the cesium salt comprising reacting an abscisic acid analog with cesium hydroxide, cesium bicarbonate or cesium carbonate in aqueous solution. In another embodiment, the invention is directed to a method of preparation of the tetramethylammonium salt comprising reacting an abscisic acid analog with a chemically equivalent amount of tetramethylammonium hydroxide in aqueous solution. In another embodiment, the invention is directed to a method of preparation of the tetrabutylammonium salt comprising reacting an abscisic acid analog with a chemically equivalent amount of tetrabutylammonium hydroxide in aqueous solution. In another embodiment, the invention is directed to a method of preparation of the choline salt comprising reacting an abscisic acid analog with choline hydroxide in aqueous solution. In yet another embodiment, the invention is directed to a method of preparation of the tetramethylguanidinium salt comprising reacting an abscisic acid analog with one chemical equivalent of tetramethylguanidine in water.

A further embodiment of the invention includes mixtures comprising combinations of salts of the abscisic acid analog prepared with alkali metal cations of high molecular weight or large steric bulk with an effective amount of a component or multiple components that enhance the long-term chemical stability of the analog and the mixture as a whole. These include but are not limited to citric acid or one of its water-soluble salts, sulfur dioxide or a water soluble bisulfite or sulfite salt.

A further embodiment of the invention includes mixtures comprising combinations of salts of abscisic acid analogs prepared with alkali metal cations of high molecular weight or large steric bulk with a substantial amount of another salt or component or multiple components which enhance the biological activity of the abscisic acid analog, including but not limited to iodide salts such as rubidium iodide, cesium iodide, choline iodide or other tetraalkylammonium iodide, or quanidine salts such as guanidine thiocyanate or tetramethylguanidinium iodide, or a surfactant. Preferred surfactants are gel-forming constituents, such as members of the Brij family.

The disclosed embodiments are simply exemplary embodiments of the inventive concepts disclosed herein and should not be considered as limiting, unless the claims expressly state otherwise.

DETAILED DESCRIPTION OF THE INVENTION

The present invention relates to aqueous liquid compositions of salts of abscisic acid analogs prepared with alkali metal cations of high molecular weight or large steric bulk. Abscisic acid analogs are structural derivatives of 2-cis-,4-trans-(S)-(+)-abscisic acid, whose structure is set forth below:

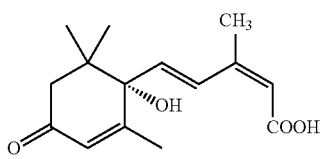

The tertiary alcohol in these compounds typically defines a chiral center for the molecule so that (R)-, and (S)-structural variants or enantiomers as well as (R,S)-racemic mixtures are possible. The liquid compositions of the present invention may utilize either the (R)-, or (S)-enantiomer or the (R,S)-racemic mixture of any selected abscisic acid analog.

For the purposes of this Application, abscisic acid analogs are defined by Structures 1, 2 and 3, wherein for Structure 1:
the bond at the 2-position of the side chain is a cis- or trans-double bond,
the bond at the 4-position of the side chain is a trans-double bond or a triple bond,
the stereochemistry of the alcoholic hydroxyl group is S-, R- or an R,S-mixture,
the stereochemistry of the $R_1$ group is in a cis-relationship to the alcoholic hydroxyl group, and
$R_1$ is ethynyl, ethenyl, cyclopropyl or trifluoromethyl.

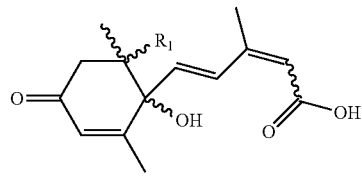

Structure 1

For PBI-376, $R_1$ is ethenyl.
For PBI-524, $R_1$ is ethynyl.
For PBI-697, $R_1$ is cyclopropyl.
For Structure 2:
the bond at the 2-position of the side chain is a cis- or trans-double bond,
the bond at the 4-position of the side chain is a triple bond, and
the stereochemistry of the alcoholic hydroxyl group is S-, R- or an R,S-mixture.

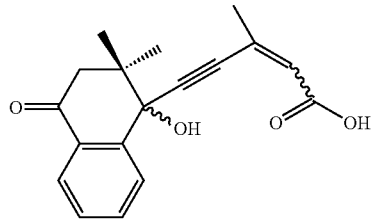

Structure 2

For Structure 3:
the bond at the 2-position of the side chain is a cis- or trans-double bond,
the bond at the 4-position of the side chain is a trans-double bond, and
the stereochemistry of the alcoholic hydroxyl group is S-, R- or an R,S-mixture.

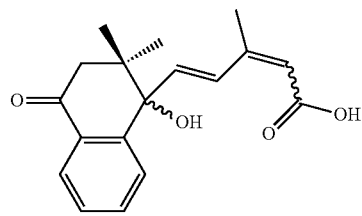

Structure 3

In one aspect, the present invention relates to a concentrated aqueous composition for the treatment of plants comprising an effective amount of at least one salt of an analog of abscisic acid prepared with alkali metal cations of high molecular weight or large steric bulk, wherein the concentration of the salt is at least 0.5% by weight of said salt.

As used herein, all numerical values relating to amounts, weight percentages and the like, are defined as "about" or "approximately" each particular value, namely, plus or minus 10%. For example, the phrase "at least 5% by weight" is to be understood as "at least 4.5% to 5.5% by weight." Therefore, amounts within 10% of the claimed values are encompassed by the scope of the claims.

The phrase "effective amount" of a salt means a sufficient amount of the salt to provide the desired biological or chemical effect without at the same time causing additional toxic effects. The amount of salt or other formulation component that is "effective" will vary from composition to composition, depending on the particular agricultural use, the particular salt or salts, and the like. Thus, it is not always possible to specify an exact "effective amount." However, an appropriate "effective amount" in any individual case may be determined by one of ordinary skill in the art using routine experimentation.

Liquid compositions of the present invention can be prepared as either ready-to-use dilutions or dilutable concentrates. According to the present invention, a solution containing from 0.5% to as much as 50% by weight of abscisic acid analog can be obtained. The dilutable concentrates can be diluted into water directly to a final application concentration or to any intermediate dilution, without risk of precipitation of the active ingredient. The aqueous formulations according to the present invention are inexpensive to manufacture, safe to handle and use, and the abscisic acid analog active ingredient is stable under storage and shipping conditions. With the compositions of the present invention there is no risk of fire as there might be with liquid formulations containing a flammable or combustible organic solvent. There is no risk of contributing to the formation of atmospheric pollution or smog as there is with formulations containing a volatile organic solvent. The aqueous formulations of the present invention are less toxic to humans or animals than similar formulations containing an organic solvent. A person having ordinary skill in the art would be able to determine how to prepare the final aqueous solution concentration for direct application to plants, or how to prepare any intermediate dilutions for use in chemigation equipment or injection diluters or similar equipment, without undue experimentation, without any chance of causing precipitation of the active ingredient, and without long and laborious stirring to bring the active ingredient into solution.

The aqueous solution formulations of the present invention may also optionally include an effective amount of an additional ingredient or several additional ingredients in order to enhance the long-term chemical stability of the abscisic acid analog or of the formulation as a whole. Such enhancing ingredients include but are not limited to citric acid or one of its water-soluble salts, sulfur dioxide or a water soluble bisulfite or sulfite salt. The use of water as the solvent allows for a combined liquid formulation comprising any or several of these inorganic components that may comprise a level of the enhancing ingredient equal to the concentration of the abscisic acid analog salt or higher, if desired.

The aqueous solution formulations of the present invention may also optionally include a substantial amount of an additional ingredient or several additional ingredients in order to enhance the biological activity of the abscisic acid analog. These activity-enhancing ingredients may include iodide salts such as rubidium iodide, cesium iodide, choline iodide or another tetraalkylammonium iodide, or a guanidine salt such as guanidine thiocyanate or tetramethylguanidinium iodide The use of water as the solvent allows for a combined liquid formulation comprising any or several of these inorganic components or organic salts that may comprise a level of the enhancing ingredient equal to the concentration of the abscisic acid analog salt or even up to 10 times the amount of abscisic acid analog by weight or more. Again, this provides an advantage over the use of an organic solvent, in which these inorganic components or organic salts may have little if any solubility.

Additionally, the aqueous solution formulations of the present invention may optionally include a substantial amount of a surfactant, in an amount equal by weight to the content of abscisic acid analog salt or even several times greater. Examples of surfactants that may be incorporated into the compositions of the present invention include, but are not limited to products of the Brij family of polyoxyethylene fatty alcohol ethers (available from Uniquema, Castle Del.), products of the Tween family of polyoxyethylene sorbitan esters (available from Uniquema, Castle Del.), products of the Silwet family of organosilcones (available from Union Carbide, Lisle Ill.), products of the Triton family of alkylphenol ethoxylates (available from Dow Chemical Company, Midland Mich.), products of the Tomadol family of ethoxylated linear alcohols (available from Tomah3 Products, Inc., Milton Wis.), products of the Myrj family of polyoxyethylene fatty acid esters (available from Uniquema Castle Del.), products of the Trylox family of ethoxylated sorbitol and ethoxylated sorbitol esters (available from Cognis Corporation, Cincinnati Ohio), or any of the specific commercial products Latron B-1956 (available from Rohm & Haas, Philadelphia Pa.), Capsil (available from Aquatrols, Paulsboro N.J.), Agral 90 (available from Norac Concepts, Inc., Orleans ON, Canada), Kinetic (available from Setre, Memphis Tenn.), or Regulaid (available from KALO, Overland Park Kans.). The presently preferred surfactants are those of the Brij or Tween families. The most preferred surfactants for inclusion in compositions of the present invention are Brij 98, Brij 78, Tween 20 and Tween 40. The concentration of surfactant in the compositions of the invention may range from about 0.02% up to about 40%. The preferred range of concentrations for the surfactant in the compositions of the invention is from about 0.1% to 30%. The most preferred range of concentrations for the surfactant in the compositions of the invention is from 0.5% to 25%. The surfactant may be included in the compositions of the present invention either together with any one or more of the inorganic salt or urea activity enhancing ingredients or in the absence of any of them.

The end user can apply compositions of the present invention to plants for various purposes, such as improving stress tolerance, reducing their water utilization, slowing their growth rate, adjusting flowering phase, for seed treatment, preventing preharvest fruit and flower drop and improving the quality and color of fruits. The possible uses may also include, for example, distribution and sale of various concentrated solutions of abscisic acid analogs. Utilizing such high concentrations for shipping and handling allows the use of smaller volumes of water, thus simplifying shipping and handling procedures and decreasing costs. The end user could then dilute the product to a 1% concentration (or other percentage depending on the end user's needs) and fill the supply reservoir of mixing equipment for spray or drench application to ornamental bedding plants ready for shipment. Alternatively, another end user could prepare a diluted solution for injection into the drip irrigation system for a vineyard at the appropriate time to enhance the color or phenolic content of a wine or table grape crop.

The present invention is also directed to methods of preparation of aqueous compositions comprising salts of an abscisic acid analog prepared with alkali metal cations of high molecular weight or large steric bulk. In one embodiment, the invention is directed to a method of preparation of the rubidium salt of the abscisic acid analog comprising reacting the abscisic acid analog with a chemically equivalent amount of rubidium hydroxide, rubidium bicarbonate or rubidium carbonate in aqueous solution. In another embodiment, the invention is directed to a method of preparation of the cesium salt comprising reacting an abscisic acid analog with cesium hydroxide, cesium bicarbonate or cesium carbonate in aqueous solution. In another embodiment, the invention is directed to a method of preparation of the tetramethylammonium salt comprising reacting an abscisic acid analog with a chemically equivalent amount of tetramethylammonium hydroxide in aqueous solution. In another embodiment, the invention is directed to a method of preparation of the tetrabutylammonium salt comprising reacting an abscisic acid analog with a chemically equivalent amount of tetrabutylammonium hydroxide in aqueous solution. In another embodiment, the invention is directed to a method of preparation of the choline salt comprising reacting an abscisic acid analog with choline hydroxide in aqueous solution. In yet another embodiment, the invention is directed to a method of preparation of the tetramethylguanidinium salt comprising reacting an abscisic acid analog with one chemical equivalent of tetramethylguanidine in water.

In a preferred embodiment, at least about 0.25% by weight of Tween-20, a detergent polysorbate, is added to the reaction mixture and resulting formulation when preparing the abscisic acid analog salts.

In another preferred embodiment, the aqueous solution comprises an antimicrobial agent to prevent microbial growth during long-term storage. The presently most preferred antimicrobial agent is potassium sorbate. When the aqueous solution of an abscisic acid analog salt of the present invention is intended for long term storage or for distribution and commercial sale to the user, it is advantageous to incorporate the antimicrobial agent at a concentration of from 0.01% to 1.0% by weight.

In another preferred embodiment, the aqueous solution comprises an agent to prevent undesirable development of coloration or appearance of precipitate during long-term storage. The presently most preferred agents for this purpose are sodium or potassium citrate and sodium or potassium sulfite or bisulfite.

In the preferred embodiments, the pH of the concentrated compositions of the invention and any aqueous solutions at final use dilution prepared from the concentrates are both approximately neutral (near pH 7).

Preferred compositions of the present invention comprise from 0.5 to 50 weight % of abscisic acid analog prepared with alkali metal cations of high molecular weight or large steric bulk in the form of a salt, from 0.01 to 1.0 weight % of an antimicrobial agent, optionally from 0.01 to 5% of a stability enhancing agent, optionally from 0.25 to 35 weight % of a surfactant, optionally from 1 to 50 weight % of another activity enhancing component, with the balance being water.

The following examples are intended to illustrate the present invention and to teach one of ordinary skill in the art how to make and use the invention. They are not intended to limit the invention or its protection in any way.

EXAMPLES

Example 1

Preparation of an Aqueous Solution Composition of the Cesium Salt of Abscisic Acid Analog PBI-524 Comprising Potassium Sorbate, Sodium Citrate and Sodium Metabisulfite A solution was prepared comprising 50 mg potassium sorbate, 20 mg of Tween-20, 100 mg of trisodium citrate dihydrate and 50 mg of sodium metabisulfite in 10 mL of water. After adding 1.09 g of abscisic acid analog PBI-524 (92% purity) the mixture was stirred for a few minutes to achieve a homogeneous suspension. A 50% aqueous solution of cesium hydroxide was added dropwise until all the abscisic acid analog was in solution. The solution was transferred to a tared brown plastic bottle and made up to a final total weight of 20 g.

Accordingly, an aqueous solution composition was prepared comprising 5% by weight abscisic acid analog PBI-524 as the cesium salt, and further comprising sodium citrate, sodium bisulfite and a naturally-occurring antimicrobial preservative.

Example 2

Preparation of an Aqueous Solution Composition of the Tetramethylguanidinium Salt of Abscisic Acid Analog PBI-524 Comprising Potassium Sorbate, Sodium Citrate and Sodium Metabisulfite A solution was prepared comprising 50 mg potassium sorbate, 20 mg of Tween-20, 100 mg of trisodium citrate dihydrate and 50 mg of sodium metabisulfite in 10 mL of water. After adding 1.09 g of abscisic acid analog PBI-524 (92% purity) the mixture was stirred for a few minutes to achieve a homogeneous suspension. Tetramethylguanidine was added dropwise with stirring until all the abscisic acid analog was dissolved. The solution was transferred to a tared brown plastic bottle and made up to a final total weight of 20 g.

Accordingly, an aqueous solution composition was prepared comprising 5% by weight abscisic acid analog PBI-524 as the tetramethylammonium salt, and further comprising sodium citrate, sodium bisulfite and a naturally-occurring antimicrobial preservative.

Comparative Example 3

Preparation of an Aqueous Solution Composition of the Ammonium Salt of Abscisic Acid Analog PBI-524 Comprising Potassium Sorbate 1.09 g of abscisic acid analog PBI-524 (92% purity) was combined with 20 mg of Tween-20 and 50 mg of potassium sorbate in 10 mL of water and stirred for a few minutes to achieve a smooth suspension. Ammonia was added in the form of a 1+9 dilution of commercial concentrated product as a titration to bring all of the solid into solution. The mixture was made up on a balance to a total weight of 20 g by adding water, and it was transferred to a brown bottle for storage.

Accordingly, an aqueous solution composition was prepared comprising 5% by weight abscisic acid analog PBI-524 as the ammonium salt, and further comprising a naturally-occurring antimicrobial preservative.

Comparative Example 4

Preparation of an Aqueous Solution Composition of the Ammonium Salt of Abscisic Acid Analog PBI-524 Comprising Potassium Sorbate, Sodium Citrate and Sodium Metabisulfite A solution was prepared comprising 50 mg potassium sorbate, 20 mg of Tween-20, 100 mg of trisodium citrate dihydrate and 50 mg of sodium metabisulfite in 10 mL of water.

After adding 1.09 g of abscisic acid analog PBI-524 (92% purity) the mixture was stirred for a few minutes to achieve a homogeneous suspension. Ammonia was added in the form of a 1+9 dilution of commercial concentrated product as a titration to bring all of the solid into solution. The mixture was made up on a balance to a total weight of 20 g by adding water, and it was transferred to a brown bottle for storage.

Accordingly, an aqueous solution composition was prepared comprising 5% by weight abscisic acid analog PBI-524 as the ammonium salt, and further comprising sodium citrate, sodium bisulfite and a naturally-occurring antimicrobial preservative.

Preparation of plant specimens for use in the treatment studies of Examples 5 through 9 that follow was carried out as follows. Tomato (variety: Rutgers) seeds were sown in an 18-cell flat filled with Promix PGX (available from Premier Horticulture Inc., Quakertown Pa.) and grown for 3 weeks to allow for germination and initial growth. Plants were then transplanted into pots (18 cm in diameter and 18 cm in height), filled with Promix BX (available from Premier Horticulture Inc., Quakertown Pa.), and grown for one or two more weeks before treatment, depending on temperature and available light. Plants received daily irrigation and weekly fertilizer (1 g/L all purpose fertilizer 20-20-20, available from The Scotts Company, Marysville, Ohio).

All treatment solutions were made up with distilled water. The abscisic acid analog PBI-524 (92% active ingredient) was obtained from the Plant Biotechnology Institute, Saskatoon, Saskatchewan Canada.

Each experiment was conducted using a randomized complete block experimental design. Solutions of the abscisic acid analog and blank treatments (plain water) were applied by spray to the aerial parts of the tomato plants at the rate of 24 mL per 6 plants. Plants were then placed in a transparent chamber with humidity controlled within the range of 40 to 60% relative humidity. Leaf transpiration rates were measured at 1, 2, 3, 4 and 7 days after treatment. Measurements of transpiration rate were conducted using a LI-1600 Steady State Porometer (LI-Cor, Lincoln, Nebr.). Each day the transpiration rate of the plants of each treatment group was normalized to a percentage of the transpiration rate of untreated plants (plants sprayed with water only) in order to control for day-to-day variability in plant status caused by changes of environmental conditions such as light intensity and temperature. Data of each plant was also averaged over a 3-day or 7-day period to balance the short term and long term effect of the abscisic acid analog on tomato leaf transpiration or growth as well as to reduce experimental variability.

Comparative Example 5

The effect of abscisic acid analog PBI-524 itself, in comparison with the effects of the corresponding ammonium salts in the compositions of Examples 3 and 4, was studied in an assay measuring tomato leaf transpiration rate (Table 1). The aqueous solution compositions of the Examples were each diluted with water to a final application concentration of 25 ppm (based on abscisic acid analog content) to match the abscisic acid analog (non-salt) standard treatment.

TABLE 1

Effect of abscisic acid analog and prior art ammonium salt compositions of Examples 3 and 4 with or without Brij 98 on tomato leaf transpiration.

| Treatment | Transpiration rate (% of control) Days after treatment | | | | | |
|---|---|---|---|---|---|---|
| | 1 | 2 | 3 | 4 | 7 | 7-Day Average |
| Untreated control (water only) | 100.00 | 100.00 | 100.00 | 100.00 | 100.00 | 100.0 |
| 25 ppm analog PBI-524 | 93.31 | 84.64 | 88.95 | 71.44 | 91.50 | 86.0 |
| 25 ppm analog PBI-524 + 0.05% Brij 98 | 48.41 | 52.45 | 54.63 | 51.55 | 84.86 | 58.4 |
| 25 ppm abscisic acid analog PBI-524 salt composition of Example 3 | 87.34 | 75.59 | 81.30 | 70.98 | 91.55 | 81.4 |
| 25 ppm abscisic acid analog PBI-524 salt composition of Example 3 + 0.05% Brij 98 | 39.03 | 52.77 | 56.28 | 51.10 | 82.74 | 56.4 |
| 25 ppm abscisic acid analog PBI-524 salt composition of Example 4 | 82.25 | 84.35 | 80.69 | 71.09 | 92.73 | 82.2 |
| 25 ppm abscisic acid analog PBI-524 salt composition of Example 4 + 0.05% Brij 98 | 49.73 | 51.98 | 51.94 | 53.66 | 81.66 | 57.8 |

Accordingly, it has been demonstrated that the ammonium salt compositions of abscisic acid analog BPI-524 are approximately as efficacious biologically as the abscisic acid analog PBI-524 itself is. There is no decrease and no useful enhancement in the biological activity obtained by conversion of the abscisic acid analog to the corresponding ammonium salt as in the compositions of Comparative Examples 3 and 4.

Example 6

The effect of abscisic acid analog formulation of Example 1 of the present invention was compared with the effect of the abscisic acid analog ammonium salt, as prepared in Example 4, in an assay measuring tomato leaf transpiration rate (Tables 2 and 3). The aqueous solution compositions of the Examples were each diluted with water to a final application concentration of 25 ppm (based on abscisic acid analog content).

TABLE 2

Effect on tomato transpiration inhibition by abscisic acid analog
PBI-524 salt compositions of Example 4 and Example 1
and the combination of Example 1 with Brij 98.

| Treatment | Transpiration rate (% of control) Days after treatment | | | | | Average of 7 days results |
|---|---|---|---|---|---|---|
| | 1 | 2 | 3 | 4 | 7 | |
| Control | 100.0 | 100.0 | 100.0 | 100.0 | 100.0 | 100.0 |
| 25 ppm abscisic acid analog as the ammonium salt composition of Example 4 (0.1 mg) | 80.8 | 78.9 | 85.7 | 91.0 | 95.5 | 86.4 |
| 25 ppm abscisic acid analog as the cesium salt composition of Example 1 (0.1 mg) | 74.6 | 72.8 | 81.7 | 83.5 | 89.1 | 80.4 |
| 25 ppm abscisic acid analog as the cesium salt composition of Example 1 (0.1 mg) + 0.05% Brij 98 | 46.1 | 64.6 | 73.7 | 77.9 | 87.2 | 69.9 |

TABLE 3

Relative potency of abscisic acid analog PBI-524
salt formulations of Example 4 and
Example 1 on tomato leaf transpiration inhibition

| Abscisic acid analog dose (mg) | Log[Abscisic acid analog] | Transpiration rate (% of control) Average of 3 days after treatment | |
|---|---|---|---|
| | | Abscisic acid analog PBI-524 as the ammonium salt composition of Comparative Example 4 | abscisic acid analog PBI-524 as the cesium salt composition of Example 1 |
| 0.03 | −1.52 | 92 | 85 |
| 0.10 | −1.00 | 82 | 76 |
| 0.30 | −0.52 | 73 | 66 |
| 1.00 | 0.00 | 63 | 56 |
| Equation | | y = 63 − 18x | y = 56 − 20x |
| $R^2$ | | 1.00 | 1.00 |
| ABA analog dose to achieve 50% inhibition of transpiration (mg) | | 5.37 | 1.99 |

Accordingly, it has been demonstrated that the cesium salt of abscisic acid analog PBI-524 of the present invention is approximately 2.7 times as active biologically as the ammonium salt, a very substantial enhancement of biological activity. This is particularly surprising since the ammonium salt (Example 4) shows no useful enhancement of biological activity when compared to the analog itself, as demonstrated in Example B1, and the fact that ammonium salts are generally considered to possess properties similar to alkali metal salts.

In this experiment, the fresh weights of the aerial parts of the tomato plants were also measured at the end of the experiment, 7 days after treatments were applied, in order to assess the relative growth suppressing activity of the compositions. The results are shown in Table 4.

TABLE 4

Effect of abscisic acid analog PBI-524 salt formulations
of Example 4 and Example 1 alone and in combination
with Brij 98 on tomato shoot fresh weight

| Treatments | Fresh weight (g) 7 days after treatment |
|---|---|
| Control | 20.3 |
| 7.5 ppm abscisic acid analog as the ammonium salt composition of Example 4 (0.03 mg) | 19.7 |
| 25 ppm abscisic acid analog as the ammonium salt composition of Example 4 (0.1 mg) | 19.3 |
| 75 ppm abscisic acid analog as the ammonium salt composition of Example 4 (0.3 mg) | 18.0 |
| 250 ppm abscisic acid analog as the ammonium salt composition of Example 4 (1 mg) | 17.3 |
| 7.5 ppm abscisic acid analog as the cesium salt composition of Example 1 (0.03 mg) | 20.0 |
| 25 ppm abscisic acid analog as the cesium salt composition of Example 1 (0.1 mg) | 19.1 |
| 75 ppm abscisic acid analog as the cesium salt composition of Example 1 (0.3 mg) | 16.7 |
| 250 ppm abscisic acid analog as the cesium salt composition of Example 1 (1 mg) | 15.5 |
| 25 ppm abscisic acid analog as the cesium salt composition of Example 1 (0.1 mg) + 0.05% Brij 98 | 18.5 |

The data in Table 4 demonstrate that while the ammonium salt of the abscisic acid analog composition of Example 4 is able to retard the growth of tomato plants in a dose-dependent manner, the cesium salt of the abscisic acid analog of Example 1 of the present invention is clearly more effective in retarding the growth in a dose-dependent manner, without producing phytotoxicity. Including a surfactant in the spray solution increases the effect even further, still with no evidence of phytotoxicity at this concentration.

Example 7

The effect of abscisic acid analog formulation of Example 2 of the present invention was compared with the effect of the abscisic acid analog ammonium salt, as prepared in Example 4, in an assay measuring tomato leaf transpiration rate Table 5). The aqueous solution compositions of the Examples were each diluted with water to a final application concentration of 25 ppm (based on abscisic acid analog content).

TABLE 5

Effect on tomato transpiration inhibition by abscisic acid analog PBI-524 salt compositions of
Example 4 and Example 2 and the combination of Example 1 with Brij 98.

| Treatment | Transpiration rate (% of control) Days after treatment | | | | | Average of 7 days results |
|---|---|---|---|---|---|---|
| | 1 | 2 | 3 | 4 | 7 | |
| Control | 100.0 | 100.0 | 100.0 | 100.0 | 100.0 | 100.0 |
| 25 ppm abscisic acid analog as the ammonium salt composition of Example 4 (0.1 mg) | 79.4 | 78.2 | 82.0 | 94.5 | 96.6 | 86.1 |
| 25 ppm abscisic acid analog as the tetramethyl-guanidinium salt composition of Example 2 (0.1 mg) | 72.0 | 70.4 | 76.7 | 78.2 | 87.5 | 77.0 |
| 25 ppm abscisic acid analog as the tetramethylguanidinium salt composition of Example 2 (0.1 mg) + 0.05% Brij 98 | 58.1 | 67.3 | 73.4 | 77.3 | 81.1 | 71.4 |

TABLE 6

Relative potency of ABA analog PBI-524 salt compositions
of Example 4 and Example 2 on tomato leaf transpiration inhibition

| Abscisic acid analog dose (mg) | Log[Abscisic acid analog] | Transpiration rate (% of control) Average of 3 days after treatment | |
|---|---|---|---|
| | | ABA analog PBI-524 ammonium salt composition of Example 4 | ABA analog PBI-524 tetramethyl-guandinium salt composition of Example 2 |
| 0.03 | −1.52 | 90 | 82 |
| 0.10 | −1.00 | 80 | 73 |
| 0.30 | −0.52 | 73 | 64 |
| 1.00 | 0.00 | 67 | 48 |
| Equation | | y = 66 − 15x | y = 50 − 22x |
| $R^2$ | | 0.99 | 0.98 |
| ABA analog dose to achieve 50% inhibition of transpiration (mg) | | 11.59 | 1.00 |

Accordingly, it has been demonstrated that the tetramethylguanidinium salt of abscisic acid analog PBI-524 is approximately 12 times as active biologically as the ammonium salt, a very substantial enhancement of biological activity.

In this experiment, the fresh weights of the aerial parts of the tomato plants were also measured at the end of the experiment, 7 days after treatments were applied, in order to assess the relative growth suppressing activity of the compositions. The results are shown in Table 7.

TABLE 7

Effect of abscisic acid analog PBI-524 salt compositions of Example 4 and
Example 2 alone and in combination with Brij 98 on tomato fresh weight

| Treatments | Fresh weight (g) 7 days after treatment |
|---|---|
| Control | 35.8 |
| 7.5 ppm abscisic acid analog as the ammonium salt composition of Example 4 (0.03 mg) | 34.8 |
| 25 ppm abscisic acid analog as the ammonium salt composition of Example 4 (0.1 mg) | 33.8 |
| 75 ppm abscisic acid analog as the ammonium salt composition of Example 4 (0.3 mg) | 32.0 |
| 250 ppm abscisic acid analog as the ammonium salt composition of Example 4 (1 mg) | 29.2 |
| 7.5 ppm abscisic acid analog as the tetramethylguanidinium salt composition of Example 2 (0.03 mg) | 34.4 |
| 25 ppm abscisic acid analog as the tetramethylguanidinium salt composition of Example 2 (0.1 mg) | 33.7 |
| 75 ppm abscisic acid analog as the tetramethylguanidinium salt composition of Example 2 (0.3 mg) | 31.0 |
| 250 ppm abscisic acid analog as the tetramethylguanidinium salt composition of Example 2 (1 mg) | 27.3 |
| 25 ppm abscisic acid analog as the tetramethylguanidinium salt composition of Example 2 (0.1 mg) + 0.05% Brij 98 | 29.7 |

The data in Table 7 demonstrate that while the ammonium salt of the abscisic acid analog composition of Example 4 is able to retard the growth of tomato plants in a dose-dependent manner, the tetramethylguanidinium salt of the abscisic acid analog of Example 2 of the present invention is clearly more effective in retarding the growth in a dose-dependent manner, without producing phytotoxicity. Including a surfactant in the spray solution increases the effect even further, still with no evidence of phytotoxicity at this concentration.

Example 8

The enhancement of the effect of the abscisic acid analog ammonium salt, as prepared in Example 4, when applied in combination with the iodide salts as described in the present invention, was studied in an assay measuring tomato leaf transpiration rate (Table 4). For each treatment the aqueous solution composition of Example 4 was mixed with a solution containing the appropriate amount of the activity enhancing additive of the present invention and then diluted with water to a final application concentration of 25 ppm (based on abscisic acid analog content) to match the abscisic acid analog standard treatment (without enhancing salt).

TABLE 8

Effect of addition of choline iodide (ChI), cesium iodide (CsI) and Brij 98 on tomato leaf transpiration inhibition induced by abscisic acid analog PBI-524 as the prior art ammonium salt.

| Treatment | Transpiration rate (% of Control) Average of 3 days results |
|---|---|
| Control | 100 |
| 25 ppm abscisic acid analog as the ammonium salt composition of Example 4 (0.1 mg active ingredient per plant) | 88 |
| 25 ppm abscisic acid analog as the ammonium salt composition of Example 4 + 231 ppm ChI | 84 |
| 25 ppm abscisic acid analog as the ammonium salt composition of Example 4 + 462 ppm ChI | 78 |
| 25 ppm abscisic acid analog as the ammonium salt composition of Example 4 + 1155 ppm ChI | 72 |
| 25 ppm abscisic acid analog as the ammonium salt composition of Example 4 + 231 ppm CI + 0.05% Brij 98 | 68 |
| 25 ppm abscisic acid analog as the ammonium salt composition of Example 4 + 260 ppm CsI | 80 |
| 25 ppm abscisic acid analog as the ammonium salt composition of Example 4 + 520 ppm CsI | 74 |
| 25 ppm abscisic acid analog as the ammonium salt composition of Example 4 + 1300 ppm CsI | 66 |
| 25 ppm abscisic acid analog as the ammonium salt composition of Example 4 + 260 ppm CsI + 0.05% Brij 98 | 62 |

Thus it has been demonstrated that application of an abscisic acid analog salt in combination with either an inorganic iodide salt or in combination with an iodide salt of an organic quaternary amine, two activity-enhancing additives of the present invention, produces a substantial enhancement of the biological effect in a dose-dependent manner. It has also been demonstrated that the activity of the combination of the abscisic acid analog salt and the iodide salt can be enhanced still further by the addition of a gel-forming surfactant.

In this experiment, the fresh weights of the aerial parts of the tomato plants were also measured at the end of the experiment, 7 days after treatments were applied, in order to assess the relative growth suppressing activity of the compositions. The results are shown in Table 9.

TABLE 9

Effect on tomato shoot fresh weight by the prior art abscisic acid analog salt of Example 4 alone and in combination with activity-enhancing additives choline iodide (ChI) or cesium iodide (CsI) of this invention and also with Brij 98 in addition.

| Treatments | Fresh weight (g), average of six plants 7 days after treatment |
|---|---|
| Control | 34.9 |
| 25 ppm abscisic acid analog as the ammonium salt composition of Example 4 (0.1 mg) | 34.9 |
| 25 ppm abscisic acid analog as the ammonium salt composition of Example 4 + 231 ppm ChI | 33.9 |
| 25 ppm abscisic acid analog as the ammonium salt composition of Example 4 + 462 ppm ChI | 33.9 |
| 25 ppm abscisic acid analog as the ammonium salt composition of Example 4 + 1155 ppm ChI | 32.1 |
| 25 ppm abscisic acid analog as the ammonium salt composition of Example 4 + 231 ppm ChI + 0.05% Brij 98 | 34.0 |
| 25 ppm abscisic acid analog as the ammonium salt composition of Example 4 + 260 ppm CsI | 34.1 |
| 25 ppm abscisic acid analog as the ammonium salt composition of Example 4 + 520 ppm CsI | 33.7 |
| 25 ppm abscisic acid analog as the ammonium salt composition of Example 4 + 1300 ppm CsI | 32.1 |
| 25 ppm abscisic acid analog as the ammonium salt composition of Example 4 + 260 ppm CsI + 0.05% Brij 98 | 33.4 |

The data in Table 9 demonstrate that addition of choline iodide or cesium iodide, two of the activity-enhancing additives of the present invention, to the composition of the ammonium salt of the abscisic acid analog of Example 4 enhances its ability to retard the growth of tomato plants in a dose-dependent manner, without producing phytotoxicity. Including a surfactant in the spray solution increases the effect even further, still with no evidence of phytotoxicity at this concentration.

Example 9

The enhancement of the effect of the abscisic acid analog ammonium salt, as prepared in Example 4, when applied in combination with the iodide salts as described in the present invention, was studied in an assay measuring tomato leaf transpiration rate (Table 10). The aqueous solution compositions were each diluted with water to a final application concentration of 25 ppm (based on abscisic acid analog content) to match the abscisic acid analog standard treatment (without enhancing salt).

TABLE 10

Effect of addition of potassium iodide (KI), Guanidine thiocyanate (GT) Effect of addition of potassium iodide (KI), Guanidine thiocyanate (GT) and Brij 98 on tomato leaf transpiration inhibition induced by abscisic acid analog PBI-524 as the prior art ammonium salt.

| Treatment | Transpiration rate (% of control) Average of 3 days results |
|---|---|
| Control | 100 |
| 25 ppm abscisic acid analog as the ammonium salt composition of Example 4 (0.1 mg active ingredient per plant) | 87 |
| 25 ppm abscisic acid analog as the ammonium salt composition of Example 4 + 166 ppm KI | 84 |
| 25 ppm abscisic acid analog as the ammonium salt composition of Example 4 + 332 ppm KI | 81 |
| 25 ppm abscisic acid analog as the ammonium salt composition of Example 4 + 830 ppm KI | 88 |
| 25 ppm abscisic acid analog as the ammonium salt composition of Example 4 + 166 ppm KI + 0.05% Brij 98 | 75 |
| 25 ppm abscisic acid analog as the ammonium salt composition of Example 4 + 118 ppm GT | 84 |
| 25 ppm abscisic acid analog as the ammonium salt composition of Example 4 + 236 ppm GT | 79 |
| 25 ppm abscisic acid analog as the ammonium salt composition of Example 4 + 590 ppm GT | 74 |
| 25 ppm abscisic acid analog as the ammonium salt composition of Example 4 + 118 ppm GT + 0.05% Brij 98 | 67 |

Accordingly, it has been demonstrated that application of an abscisic acid analog salt in combination with either potassium iodide or in combination with a guanidine salt, two activity-enhancing additives of the present invention, produces an enhancement of the biological effect. The guanidine salt produces a substantial enhancement of the biological activity in a dose-dependent manner. The enhancement by potassium iodide is not as large and not as clearly dose dependent. It has also been demonstrated that the activity of the combination of the abscisic acid analog salt and either of the added salts can be enhanced still further by the addition of a gel-forming surfactant.

In this experiment, the fresh weights of the aerial parts of the tomato plants were also measured at the end of the experiment, 7 days after treatments were applied, in order to assess the relative growth suppressing activity of the compositions. The results are shown in Table 11.

TABLE 11

Effect of ABA analog salt V0367-020 and its combination with potassium iodide (KI), guanidine thiocyanate (GT) and Brij 98 on tomato shoot fresh weight

| Treatments | Fresh weight (g) 7 days after treatment |
|---|---|
| Control | 33.9 |
| 25 ppm abscisic acid analog as the ammonium salt composition of Example 4 (0.1 mg) | 33.4 |
| 25 ppm abscisic acid analog as the ammonium salt composition of Example 4 + 166 ppm KI | 32.9 |
| 25 ppm abscisic acid analog as the ammonium salt composition of Example 4 + 332 ppm KI | 31.8 |
| 25 ppm abscisic acid analog as the ammonium salt composition of Example 4 + 830 ppm KI | 33.9 |
| 25 ppm abscisic acid analog as the ammonium salt composition of Example 4 + 166 ppm KI + 0.05% Brij 98 | 31.2 |
| 25 ppm abscisic acid analog as the ammonium salt composition of Example 4 + 118 ppm GT | 33.7 |
| 25 ppm abscisic acid analog as the ammonium salt composition of Example 4 + 236 ppm GT | 32.2 |
| 25 ppm abscisic acid analog as the ammonium salt composition of Example 4 + 590 ppm GT | 31.7 |
| 25 ppm abscisic acid analog as the ammonium salt composition of Example 4 + 118 ppm GT + 0.05% Brij 98 | 31.1 |

The data in Table 11 demonstrate that addition of potassium iodide or guanidine thiocyanate, two of the activity-enhancing additives of the present invention, to the ammonium salt of the abscisic acid analog of Example 4 enhances its ability to retard the growth of tomato plants, without producing phytotoxicity. Including a surfactant in the spray solution increases the effect even further, still with no evidence of phytotoxicity at this concentration.

The invention claimed is:

1. A tetramethylguanidinium salt of an abscisic acid analog, wherein the abscisic acid analog is selected from the group consisting of the abscisic acid analogs of Structures 1, 2 and 3, wherein
   (a) for Structure 1:
      (i) the bond at the 2-position of the side chain is a cis- or trans-double bond;
      (ii) the bond at the 4-position of the side chain is a trans-double bond or a triple bond;
      (iii) the stereochemistry of the alcoholic hydroxyl group is S-, R- or an R,S-mixture;
      (iv) the stereochemistry of the $R_1$ group is in a cis-relationship to the alcoholic hydroxyl group; and
   $R_1$ is ethynyl, ethenyl, cyclopropyl or trifluoromethyl;

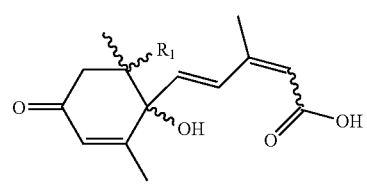

Structure 1

(b) for Structure 2;
   (i) the bond at the 2-position of the side chain is a cis- or trans-double bond;
   (ii) the bond at the 4-position of the side chain is a triple bond; and
   (iii) the stereochemistry of the alcoholic hydroxyl group is S-, R- or an R,S-mixture; and

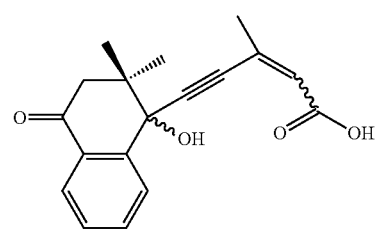

Structure 2 cc) for Structure 3:
   (i) the bond at the 2-position of the side chain is a cis- or trans-double bond;
   (ii) the bond at the 4-position of the side chain is a trans-double bond; and
   (iii) the stereochemistry of the alcoholic hydroxyl group is S-, R- or an R,S-mixture;

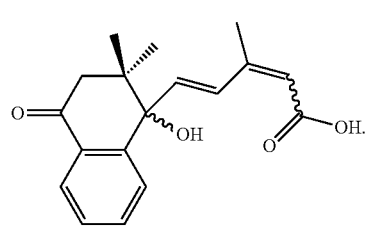

Structure 3

2. An aqueous composition for treatment of plants comprising an effective amount of the tetramethylguanidinium salt of the abscisic acid analog of claim 1, wherein the concentration of the salt is at least 0.5% by weight of said composition; an effective amount of an antimicrobial agent; an effective amount of a surfactant, optionally one or more performance enhancing additives; and optionally one or more additives to stabilize the color.

3. The composition of claim 2, wherein the concentration of the salt is at least 2% by weight of said composition.

4. The composition of claim 2 that further comprises an antimicrobial agent.

5. The composition of claim 4, wherein said antimicrobial agent is potassium sorbate.

6. The composition of claim 2 that further comprises one or more performance-enhancing additives.

7. The composition of claim 6 wherein said performance-enhancing additives are iodide salts selected from the group consisting of rubidium iodide; cesium iodide, lithium iodide and quaternary ammonium iodide of the form $R_1R_2R_3R_4N^+ I^-$, wherein $R_1, R_2, R_3$ and $R_4$ are independently lower alkyl or alkenyl of 1 to 6 carbons arranged in a straight or branched chain and comprising or joined together to form 0 or 1 ring structures and bearing 0, 1 or 2 halogens or hydroxyl groups, and wherein one or more R group may bear a phenyl substituent, or wherein said performance-enhancing additives are guanidinium salts, wherein the guanidine may bear 0 to 5 methyl or ethyl groups.

8. The composition of claim 7 wherein said performance-enhancing additive is choline iodide.

9. The composition of claim 6 wherein said performance-enhancing additive is a water soluble cesium salt other than the iodide.

10. The composition of claim 7 that further comprises one or more additives to stabilize the color.

11. The composition of claim 10 wherein said color-stabilizing additive is a sodium or potassium salt of citric acid or sodium or potassium, sulfite, bisulfite or metabisulfite.

12. An aqueous composition comprising from about 5 to about 45 weight % of the abscisic acid analog in the form of the tetramethylguanidinium salt of claim 1; from 0 to about 0.5 weight % potassium sorbate; from about 0.2 to about 1.0 weight % sodium citrate; and one or more additives to stabilize the color.

* * * * *